(12) United States Patent
Furukawa et al.

(10) Patent No.: US 11,331,318 B2
(45) Date of Patent: May 17, 2022

(54) ARTERIAL OXYGEN SATURATION DEGREE IMPROVER

(71) Applicant: FURUKAWA RESEARCH OFFICE CO., LTD., Tokyo (JP)

(72) Inventors: Satoru Furukawa, Tokyo (JP); Satoshi Odo, Kanagawa (JP)

(73) Assignee: FURUKAWA RESEARCH OFFICE CO., LTD., Tokyo (JP)

( * ) Notice: Subject to any disclaimer, the term of this patent is extended or adjusted under 35 U.S.C. 154(b) by 65 days.

(21) Appl. No.: 16/611,236

(22) PCT Filed: May 11, 2018

(86) PCT No.: PCT/JP2018/018409
§ 371 (c)(1),
(2) Date: Nov. 6, 2019

(87) PCT Pub. No.: WO2018/207929
PCT Pub. Date: Nov. 15, 2018

(65) Prior Publication Data
US 2020/0155553 A1 May 21, 2020

(30) Foreign Application Priority Data
May 12, 2017 (JP) .............................. JP2017-095664

(51) Int. Cl.
| | | |
|---|---|---|
| A61K 31/513 | (2006.01) | |
| A23L 33/10 | (2016.01) | |
| A61P 3/00 | (2006.01) | |
| A61K 31/205 | (2006.01) | |
| A61K 9/00 | (2006.01) | |

(52) U.S. Cl.
CPC ............ *A61K 31/513* (2013.01); *A23L 33/10* (2016.08); *A61K 31/205* (2013.01); *A61P 3/00* (2018.01); *A61K 9/006* (2013.01)

(58) Field of Classification Search
CPC ............................... A61K 31/513; A61P 43/00
See application file for complete search history.

(56) References Cited

FOREIGN PATENT DOCUMENTS

| | | | |
|---|---|---|---|
| JP | 2008-512381 A | 4/2008 | |
| JP | 2011-98896 A | 5/2011 | |
| JP | 2011-136907 A | 7/2011 | |
| JP | 2012-246280 A | 12/2012 | |
| JP | 2015-43743 A | 3/2015 | |
| WO | 2002/100409 A | 12/2002 | |
| WO | 2009/069291 A | 6/2009 | |

OTHER PUBLICATIONS

English Translation of JP 2012-246280 A (2012) of PTO-1449.*
Nikolova, M et al., Antihypoxic action of orotic acid, Eksperimentalna medicina i morfologija, 1981, Vo1.20, No. 3, pp. 171-176 [English summary].
Milanova, D. et al., Study on the Anti-Hypoxic Effect of Some Drugs Used in the Pharmacotherapy of Cerebrovascular Disease, Meth. and Find. Exptl. Clin. Pharmacol., 1983, vol. 5, No. 9,pp. 607-612.
Lin, Zaw et al., Uridine Preserves ATP During Hypoxic Perfusion of the Rat Heart, Asia Pacific Heart J., 1997, Vo1.6, No. 3,pp. 190-196.
Rosenfeldt, Franklin L. et al.,Mechanism of Cardioprotective Effect of Orotic Acid, Cardiovascular Drugs and Therapy, 1998 Vo1.12, pp. 159-170.
Sonnewald, Ursula et al., Effect of Orotic Acid on the Metabolism of Cerebral Cortical Astrocytes During Hypoxia and Reoxygenation:An NMR Spectroscopy Study, Journal of Neuroscience Research, 1998, vol. 51, pp. 103-108.
Sato, Nagato et al. "Prognostic significance of serum uric acid in patients with chronic obstructive pulmonary disease receiving home oxygen therapy" Department of Respiratory Medicine, Saitama Cardiovascular and Respiratory Center, 41(2) 2003. English Translation Abstract.
Sahebjami, Hamid "Changes in Urinary Uric Acid Excretion in Obstructive Sleep Apnea Before and After Therapy With Nasal Continuous Positive Airway Pressure" CHEST Journal, Jun. 1998, vol. 113, Issue 6, pp. 1604-1608.
Niijima, Kuniyuki et al. "Influence of alcohol drinking on disordered breathing and pulse rate during sleep" Translation of Journal of Occupational Health, vol. 48, 2006, p. 860.
Sato, Nobuhiro et al."Acute effect of ethanol on hemoperfusion and oxideative metabolism in the liver in vivo" Kanzo [Liver] 1981. 22/4 pp. 72-77.
Suda, Michio "Exercise and Uric Acid" Translation of Hyperuricemia and Gout, vol. 14, No. 1, 2006, p. 56.
Ogino, Kazuhide et al. "Exercise-induced Hyperuricemia and Uric Acid Metabolism" Translation of Hyperuricemia and Gout, Vo. 17, No. 2, 2009 pp. 51-52.
Internation Search Report PCT/JP2018/018409 dated Jul. 3, 2018 English Translation.

* cited by examiner

*Primary Examiner* — Kevin E Weddington
(74) *Attorney, Agent, or Firm* — Edwin S. Flores; Daniel J. Chalker; Chalker Flores, LLP (57) ABSTRACT

The present invention provides an agent that suppresses a decrease in arterial oxygen saturation or increases decreased arterial oxygen saturation, and that can be ingested by a relatively simple method and has excellent immediate effectivity and persistence. The agent of the invention comprises orotic acid or a salt thereof as an active ingredient, which is absorbed into the body via oral mucosa. When the agent is absorbed in the body via oral mucosa it suppresses a decrease in arterial oxygen saturation or increases decreased arterial oxygen saturation. The agent is effective for improvement or prevention of a symptom or disease related to a decrease in arterial oxygen saturation, such as exercise, alcohol drinking, a decrease in oxygen concentration in air, reduced cardiopulmonary function, and respiratory arrest, and a symptom or disease caused by hypoxia, in particular, for prevention of an increase in uric acid level.

12 Claims, 10 Drawing Sheets

ARTERIAL OXYGEN SATURATION DEGREE IMPROVER

CROSS-REFERENCE TO RELATED APPLICATIONS

This application is the National Stage of International Application No. PCT/JP2018/018409, filed on May 11, 2018, the content of which is incorporated by reference herein and claiming the priority of JP 2017-095664, filed on May 12, 2017.

TECHNICAL FIELD

The present invention relates to an agent for improving arterial oxygen saturation comprising orotic acid or a salt thereof (hereinafter may be referred to as "orotic acid group") as an active ingredient. The improving agent is for oral mucosa administration in which the orotic acid or a salt thereof is absorbed into the body via the oral mucosa.

BACKGROUND ART

Orotic acid (also referred to as uracil-6-carboxylic acid or vitamin B13) is a main intermediate in a pyrimidine nucleotide biosynthesis system and is derived from dihydroorotic acid by means of dihydroorotic acid dehydrogenase and is converted to orotidylic acid by means of orotic acid phosphoribosyltransferase (PRPP). The orotidylic acid is further rapidly converted to uridine monophosphate (UMP), and pyrimidine nucleotides, such as uridine triphosphate and cytidine triphosphate, are then synthesized.

In recent years, studies on physiological actions of orotic acid are being progressed. For example, it has been reported that orotic acid has a blood uric acid level-reducing action (Patent Document 1), orotic acid has an endurance-enhancing action (Patent Documents 2 and 3), and orotic acid has an action of decreasing oxygen consumption and energy consumption (Patent Document 3). However, these documents merely disclose the effects of orotic acid in animal experiments using mice or rats when the orotic acid was orally administered for relatively long periods of time (for 10 days to 3 weeks), and it has not been known that administration of orotic acid so that the orotic acid is absorbed into the body via oral mucosa suppresses a decrease in arterial oxygen saturation or expresses an effect of improving decreased arterial oxygen saturation or decreased tissue oxygen saturation.

Incidentally, in obstructive sleep apnea patients whose upper respiratory tract, which is a passage of air, is physically narrowed to stop the breathing, apnea or hypopnea is repeatedly caused during nighttime sleep, and therefore the patients are exposed to hypoxemia for a long time. Although the serum uric acid level is regulated by the balance between production and urinary excretion, it is known that under hypoxic conditions, the decomposition of ATP is promoted at the cellular level by insufficient oxygen supply and that production of uric acid, which is a terminal metabolite of purine, is enhanced (Non-patent Document 1).

If oxygen is deficient, aerobic ATP generation in the TCA cycle is impossible, and ATP is generated by glycolysis by generating lactic acid from pyruvic acid for regenerating NAD necessary for the glycolysis metabolism. As a result, lactic acid is accumulated. It is also known that if oxygen is deficient, in order to regenerate ATP, one ATP molecule and one AMP molecule are generated from two ADP molecules, and the generated AMP is decomposed and converted into uric acid. It is further known that the glycolysis is enhanced in order to compensate for ATP, and anaerobically generated lactic acid suppresses excretion of uric acid (Non-patent Documents 2 and 3).

Furthermore, it is known that in hypoxia in a chronic obstructive pulmonary disease (COPD) case, the uric acid level is increased (Non-patent Document 4), liver oxygen consumption is enhanced by alcohol intake (Non-patent Document 5), and alcohol drinking affects disordered breathing and pulse rate (Non-patent Document 6).

PRIOR ART DOCUMENTS

Patent Documents

Patent Document 1: Japanese unexamined Patent Application Publication No. 2011-98896
Patent Document 2: Japanese unexamined Patent Application Publication No. 2011-136907
Patent Document 3: Japanese unexamined Patent Application Publication No. 2012-246280

Non-Patent Documents

Non-patent Document 1: CHEST, 1998, 113, pp. 1604-1608
Non-patent Document 2: Konyosan-kessyo to Tsufu (Hyperuricemia and Gout), 14(1), 2006, pp. 55-58
Non-patent Document 3: Konyosan-kessyo to Tsufu (Hyperuricemia and Gout), 17(2), 2009, pp. 51-56
Non-patent Document 4: Annals of the Japanese Respiratory Society, 41(2), 2003, pp. 74-79
Non-patent Document 5: Kanzo (Liver), 22(4), 1981, pp. 72-77
Non-patent Document 6: Journal of Occupational Health, vol. 48, 2006, p. 860

SUMMARY OF THE INVENTION

Object to be Solved by the Invention

It is an object of the present invention to provide an improving agent that is used for suppressing a decrease in arterial oxygen saturation or increasing decreased arterial oxygen saturation or decreased tissue oxygen saturation and can be ingested by a relatively simple method and has excellent immediate effectivity and persistence.

Means to Solve the Object

The present inventors have been intensively researched to solve the above problems. During the process thereof, the inventors have found that when orotic acid or a salt thereof is administered to a subject whose arterial oxygen saturation or tissue oxygen saturation has been decreased or a subject whose arterial oxygen saturation or tissue oxygen saturation is predicted to decrease so that the orotic acid is absorbed into the body via oral mucosa, not by oral administration, the decreased arterial oxygen saturation or the decreased tissue oxygen saturation is rapidly increased, or a decrease in arterial oxygen saturation or tissue oxygen saturation is suppressed, symptoms related to the decrease in arterial oxygen saturation or tissue oxygen saturation are rapidly improved, and the improved or recovered physical conditions (state) are then stably maintained, and the present invention has been accomplished.

That is, the present invention provides the followings:

[1] An agent for improving arterial oxygen saturation for oral mucosa administration, the agent comprising orotic acid or a salt thereof as an active ingredient, wherein the agent is used for suppressing a decrease in arterial oxygen saturation or for increasing decreased arterial oxygen saturation; and the orotic acid or a salt thereof is absorbed into the body via oral mucosa;

[2] The agent according to aspect [1], wherein the decrease in arterial oxygen saturation is caused by breathing in air with reduced oxygen concentration, reduced cardiopulmonary function, or respiratory arrest;

[3] The agent according to aspect [1], wherein the decrease in arterial oxygen saturation is caused by exercise;

[4] The agent according to aspect [1], wherein the decrease in arterial oxygen saturation is caused by alcohol drinking;

[5] The agent according to any one of aspects [1] to [4], wherein the orotic acid or a salt thereof is comprised in admixture with carnitine;

[6] The agent according to any one of aspects [1] to [5], wherein the improver is a sublingual tablet;

[7] The agent according to any one of aspects [1] to [6], wherein the orotic acid or a salt thereof is administered at a dose of 200 mg/day;

[8] An agent for preventing for an increase in blood uric acid level, the agent for improving comprising the arterial oxygen saturation for oral mucosa administration according to any one of aspects [1] to [7] as an active ingredient; and

[9] An agent for preventing or ameliorating a disease related to a decrease in arterial oxygen saturation, the agent comprising the agent for improving arterial oxygen saturation for oral mucosa administration according to any one of aspects [1] to [7] as an active ingredient.

Other aspects of the present invention include [10] a method for suppressing a decrease in arterial oxygen saturation or increasing decreased arterial oxygen saturation, the method comprising administration of orotic acid or a salt thereof that can be absorbed into the body via oral mucosa to a subject whose arterial oxygen saturation may decrease or a subject whose arterial oxygen saturation has decreased so that the orotic acid or a salt thereof is absorbed into the body via oral mucosa; [11] orotic acid or a salt thereof to be used as an agent for oral mucosa administration for suppressing a decrease in arterial oxygen saturation or increasing decreased arterial oxygen saturation; and [12] a use of orotic acid or a salt thereof for manufacturing an agent for improving for oral mucosa administration for suppressing a decrease in arterial oxygen saturation or increasing decreased arterial oxygen saturation.

Effect of the Invention

The agent for improving arterial oxygen saturation the present invention is a prophylactic or ameliorating agent for a symptom or disease caused by hypoxia. For example, when orotic acid or a salt thereof is administered to a subject, before exercise or alcohol drinking, whose arterial oxygen saturation may be decreased so that the orotic acid or a salt thereof is absorbed into the body via oral mucosa (for example, sublingual administration), the arterial oxygen saturation is suppressed from decreasing; alternatively, when orotic acid or a salt thereof is administered to a subject, after excise or alcohol drinking, whose arterial oxygen saturation has been decreased so that orotic acid or a salt thereof is absorbed into the body via oral mucosa (for example, sublingual administration), the decreased arterial oxygen saturation or decreased tissue oxygen saturation is rapidly increased, the decrease in arterial oxygen saturation and the symptom related to tissue hypoxia are rapidly improved (immediate effectivity), the recovered physical condition or state is stably maintained for a long time (persistence), and the decrease in arterial oxygen saturation and the symptom related to tissue hypoxia can be suppressed (prevented or improved) for a long time. In the present invention, such excellent immediate effectivity and persistence of orotic acid or a salt thereof are exhibited when the orotic acid or a salt thereof is administered so that it is absorbed into the body via oral mucosa, not by oral administration.

MODE OF CARRYING OUT THE INVENTION

The improving agent of the present invention is an agent for improving arterial oxygen saturation whose application (purpose of use) is specified to "suppression of a decrease in arterial oxygen saturation or increase of decreased arterial oxygen saturation" and whose application (dosage form) is specified to "oral mucosa administration" and comprises orotic acid or a salt thereof as an active ingredient, and is characterized in that the orotic acid or a salt thereof is administered so that it is absorbed into the body via oral mucosa. In addition, the "prophylactic agent for an increase in blood uric acid level" and "prophylactic or ameliorating agent for a disease related to a decrease in arterial oxygen saturation" of the present invention comprising the improving agent of the present invention as an active ingredient. These improving agent, prophylactic agent, and prophylactic or ameliorating agent of the present invention are used as pharmaceutical products (pharmaceutical compositions), health foods (such as functional foods, nutritional supplements, health supplements, nutrition-enriched foods, nutritionally balanced foods, and supplements) to be consumed for the purpose of maintaining health, or foods with health claims (such as foods for specified health uses, foods with nutrient function claims, and foods with function claims).

The "arterial oxygen saturation (SpO2)" in the present invention is an index showing the level of oxygen contained in blood. SpO2 indicates what percentage of many hemoglobins in (artery) blood carry oxygen and can be measured using a simple device called a pulse oximeter.

In the present specification, a "decrease in arterial oxygen saturation" means a state in which the arterial oxygen saturation (SpO2) is decreased to a level lower than the normal level by any factor, and a state in which the lactic acid level or the uric acid level in blood is increased to a level higher than the normal level by oxygen deficiency in the body tissues, such as muscle, liver, and brain, is also included in the "decrease in arterial oxygen saturation" for convenience. In addition, a decrease in oxygen saturation preferably means a state in which the oxygen saturation is at least 2% lower than the normal level. The normal level of SpO2 varies depending on the regular state of each subject and therefore cannot be specified unconditionally but is usually at least 93% or more, preferably at least 94%, further preferably at least 95%, and most preferably at least 96% or more. Accordingly, the "decrease in arterial oxygen saturation" includes, for example, a SpO2 level of 70% or more and less than 96%, 80% or more and less than 96%, and 90% or more and less than 96%.

In the present specification, "increasing decreased arterial oxygen saturation" means that the level of SpO2 in arterial blood decreased to a level lower than the normal level is increased or that the oxygen deficient state of tissues, such as brain and liver, is improved.

The causes of decreasing the SpO2 level in arterial blood or tissues, such as brain and liver, to a level lower than the normal level (causing oxygen deficiency) are, symptoms or diseases resulted from oxygen deficiency in the body due to some causes, for example, exercise (for example, mountain climbing, swimming, long distance running [marathon], short distance running, skating competition, sacker, basketball, tennis, and bicycle racing), blood flow deficiency by any factor, a decrease in oxygen concentration in air (for example, high mountain, high-altitude training, hypoxic training, and insufficient ventilation in closed space), anaerobic state, decreased lung function (for example, chronic obstructive pulmonary disease [COPD], asthma, idiopathic pulmonary fibrosis, and aging), and respiratory arrest (for example, sleep apnea syndrome and conscious respiratory arrest during diving), and a specific cause is not identified. Examples of the cause other than the above include dysesthesia, numbness, dyspnea, decreasing of constitution, stiff shoulders, headache, fatigue, poor concentration, glaucoma, epilepsy, respiratory acidosis in, e.g., pulmonary emphysema, decubitus, cardiac edema, hepatic edema, premenstrual tension, Meniere's disease syndrome, cardiovascular diseases (for example, hypertension, arrhythmia, angina, myocardial infarction, stroke, and cerebrovascular disorder), diabetes, frequent urination, rash, fever, dementia, and alcohol drinking. Among these causes, the improving agent of the present invention is especially effective to a decrease in oxygen concentration in air, a decreased lung function, respiratory arrest, exercise, and alcohol drinking.

The "decrease in oxygen concentration in air" means a condition (state) in which the oxygen concentration in air is lower than the normal level (about 21%). An example of the symptom or disease related to such a decrease in oxygen concentration in air is altitude sickness.

Since it is known that the blood uric acid level is increased by hypoxia (Non-patent Document 4), when a decrease in SpO2 (tissue oxygen deficiency) is caused by an increase in blood uric acid level, for example, in exercise or alcohol drinking, a decrease in SpO2 is suppressed (tissue oxygen deficiency is improved) or decreased SpO2 level is increased (cancellation of tissue oxygen deficiency) by absorption of the improving agent or prophylactic agent for an increase in blood uric acid level of the present invention into the body via oral mucosa, and as a result, an increase in blood uric acid level can be suppressed.

In the present specification, an "increase in blood uric acid level" means that the uric acid concentration in blood, plasma, or serum is increased to a level higher than the normal level. The normal level of blood uric acid concentration varies depending on the sex and the regular state of each subject and therefore cannot be specified unconditionally but is usually within a range of 2.0 to 7.0 mg/dL and preferably 3.8 to 7.0 mg/dL when the subject is a man and preferably 2.4 to 5.8 mg/dL when the subject is a woman.

In high-altitude training or hypoxic training, the decrease in arterial oxygen saturation is suppressed or the decreased arterial oxygen saturation is increased by absorption of the improving agent of the present invention into the body via oral mucosa. As a result, it can be expected that the training is efficiently performed to improve the performance of a sport for which high-altitude training or hypoxic training is effective.

Examples of the sport for which high-altitude training or hypoxic training is effective include sports (exercise), such as mountain climbing, swimming, marathon, short distance running, skating competition, sacker, basketball, tennis, and bicycle racing.

The improving agent, the prophylactic agent, and the prophylactic or ameliorating agent of the present invention may have any shape or form as long as orotic acid or a salt thereof is absorbed into the body via oral mucosa, and the shape or the form and the system for being retained in the oral cavity are not particularly limited. The improving agent, the prophylactic agent, and the prophylactic or ameliorating agent of the present invention preferably have an action of retaining the administered orotic acid or a salt thereof in the oral cavity for a long time by that the surface of the improving agent of the present invention is gradually dissolved by saliva and disappears (sustained release agent applied to oral mucosa) for retarding the release of orotic acid or a salt thereof. In addition, the size, shape, etc. of the improving agent, the prophylactic agent, or the prophylactic or ameliorating agent of the present invention are preferably adjusted not to be quickly swallowed.

Examples of the shape or form of the sustained release agent applied to oral mucosa include troches, sublingual tablets, buccal tablets, granules wrapped in an edible film such as wafer paper (edible starch film), jelly tablets, and chewable tablets. In the granules wrapped in an edible film, in order to improve the absorbability of orotic acid or a salt thereof into oral mucosa, the orotic acid or a salt thereof can be used in admixture with powder of an ingredient that increases the solubility of orotic acid or a salt thereof described below. When the absorbability of orotic acid or a salt thereof into oral mucosa is enhanced without using the ingredient that increases the solubility of orotic acid or a salt thereof, fine powder of the orotic acid or a salt thereof finely pulverized to 5 µm or less may be used.

In the sustained release agent applied to oral mucosa, the time that orotic acid or a salt thereof stays in the oral cavity after administration can be appropriately selected according to, for example, the dose of orotic acid or a salt thereof and the age, weight, sex, symptom, and sensitivity to the orotic acid or a salt thereof of each subject to whom the agent is administered, and is, for example, at least 10 seconds, preferably at least 15 seconds, more preferably at least 20 seconds, further preferably at least 25 seconds, and most preferably at least 30 seconds.

Since the orotic acid or a salt thereof as an active ingredient of the improving agent, the prophylactic agent, or the prophylactic or ameliorating agent of the present invention can be constituted as a safe food ingredient and is also inexpensive, the orotic acid or a salt thereof can be ingested easily and continuously on a daily basis. Consequently, the improving agent, the prophylactic agent, or the prophylactic or ameliorating agent of the present invention is preferably a food or supplement. Such a food is not particularly limited. For example, when the food is in a shape or a form of a sustained release agent to be applied to oral mucosa, examples of the food include (throat) candy, chewing gum, gummi candy, jelly, chewing candy, and jellybeans.

The orotic acid includes orotic acid hydrates, such as free form orotic acid monohydrate, in addition to free form orotic acid (anhydrate).

The salt of orotic acid may be any salt with a physiologically acceptable base, and examples thereof include alkali metal salts, such as sodium salts and potassium salts; alkaline earth metal salts, such as calcium salts and magnesium salts; heavy metal salts, such as zinc salts; ammonium salts; and salts with basic amino acids or basic peptides described below.

The improving agent, the prophylactic agent, or the prophylactic or ameliorating agent of the present invention preferably further comprises an ingredient (for example, amino acid or peptide) that increases the solubility of orotic acid for improving the absorbability of the orotic acid into oral mucosa. Examples of the ingredient that increases the solubility of orotic acid include lysine, histidine, arginine, ornithine, carnitine, choline, carnosine, anserine, and balenine, and among these ingredients, carnitine is a suitable example. The ingredients that increase the solubility of orotic acid include the L-form and the D-form thereof and a mixture thereof. In addition, the ingredients that increase the solubility of orotic acid may be used alone or in combination of two or more.

The improving agent, the prophylactic agent, and the prophylactic or ameliorating agent of the present invention may further comprise formulation ingredients, such as pharmaceutically acceptable ordinary carrier, binder, stabilizer, excipient, diluent, pH buffer, disintegrator, isotonic agent, additive, coating agent, solubilizer, lubricant, sliding agent, dissolution assisting agent, lubricating agent, flavor, sweetener, solvent, gelling agent, and nutrient, as needed. As such formulation ingredients, for example, water, physiological saline, animal fat, animal oil, vegetable oil, lactose, starch, gelatin, crystalline cellulose, gum, talc, magnesium stearate, hydroxypropyl cellulose, polyalkylene glycol, polyvinyl alcohol, and glycerol can be exemplified.

The dose of orotic acid or a salt thereof comprised in the improving agent, the prophylactic agent, or the prophylactic or ameliorating agent of the present invention is appropriately determined according to, for example, the age, weight, sex, symptom, and sensitivity to the orotic acid or a salt thereof of each subject to whom the agent is administered. The dose of orotic acid or a salt thereof is, for example, within a range of 50 to 2000 mg/day, preferably 100 to 1000 mg/day, more preferably 150 to 800 mg/day, further preferably 150 to 600 mg/day, particularly preferably 200 to 400 mg/day, and most preferably 200 mg/day. In addition, a single dose or a plurality of doses (for example, 2 to 4 times) may be administered per day. For example, when the dose of orotic acid or a salt thereof is 200 mg per day, a tablet comprising 50 mg of orotic acid or a salt thereof may be administered four times per day, a tablet comprising 100 mg of orotic acid or a salt thereof may be administered twice per day, or a tablet comprising 200 mg of orotic acid or a salt thereof may be administered once per day.

The orotic acid group may be commercial products, such as free form orotic acid monohydrate (manufactured by Kyowa Hakko Bio Co., Ltd. or manufactured by Matsumoto Trading Co., Ltd.), orotic acid anhydride (manufactured by Kyowa Hakko Bio Co., Ltd.), orotic acid monohydrate (manufactured by SIGMA-ALDRICH), and orotic acid monohydrate (manufactured by Wako Pure Chemical Industries, LTD.), or may be prepared by producing and accumulating orotic acids in the culturing medium by a fermentation process using various microorganisms introduced with mutations of pyrimidine requirement or pyrimidine analog resistance (for example, see Japanese Patent No. 2927882) and purifying and collecting the orotic acids from, for example, the culture or whey containing the orotic acids by an ordinary purification method, for example, a separation refining method, such as precipitation or chromatography using ion exchange resin or activated carbon.

The present invention will now be more specifically described by Examples, but the technical scope of the present invention is not limited to these examples.

EXAMPLES

Example 1: Effect 1 of Suppressing Decrease in Arterial Oxygen Saturation by Absorption of Orotic Acid Via Oral Mucosa A test of verifying whether absorption of orotic acid via oral mucosa has an effect of suppressing a decrease in arterial oxygen saturation or not was carried out.

[Test Method 1]

A man in his 60s (subject A) entered a normobaric hypoxic room (oxygen concentration: 12.4 to 12.7%, equivalent to that at an altitude of about 4000 m, 23° C.) of Miura Dolphins and was then administered with 400 mg of orotic acid by repeating twice a method (sublingual administration) in which a mixture (400 mg) of free form orotic acid (manufactured by Kyowa Hakko Bio Co., Ltd., 200 mg) and L-carnitine (manufactured by Lonza Japan Ltd., 200 mg) wrapped in wafer paper was placed under the tongue and allowed to stay in the mouth for at least 30 seconds, and the SpO2 and heart rate were measured using a pulse oximeter PULSOX-300i (manufactured by Konica Minolta, Inc.). Incidentally, in this example, carnitine was used for enhancing the solubility of orotic acid in water (absorbability into oral mucosa (see Japanese unexamined Patent Application Publication No. 2015-43743). Subject A was required not to consciously change his breathing after entering the room.

[Result 1]

Figure 1A:
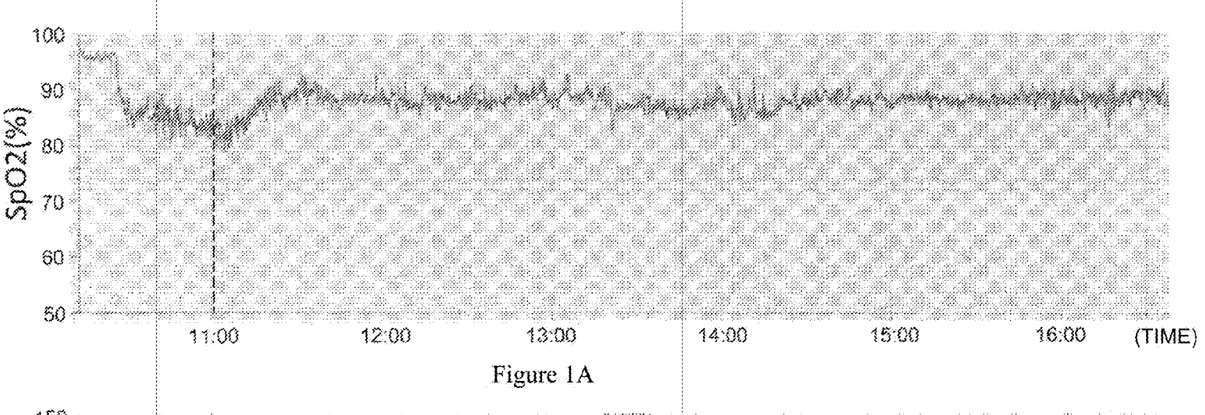
FIGS. 1A-B include graphs showing the results of measurement of transcutaneous arterial oxygen saturation (SpO2) (FIG. 1A) and heart rate (bpm) (FIG. 1B) of a subject A, where the measurement was performed in a normobaric hypoxic room before and after sublingual administration of orotic acid. The broken line in each graph indicates the time at which the orotic acid was sublingually administered.

After entering the room, the SpO2 level of subject A rapidly decreased to 83% to 84%, but the SpO2 level increased to 88% about 30 minutes after the sublingual administration (11:00 indicated by the broken line in FIG. 1A) of orotic acid (see FIG. 1A). It was shown that thereafter the SpO2 level was stably maintained at about 88% for at least 5 hours until leaving the room (see FIG. 1A).

Figure 1B:
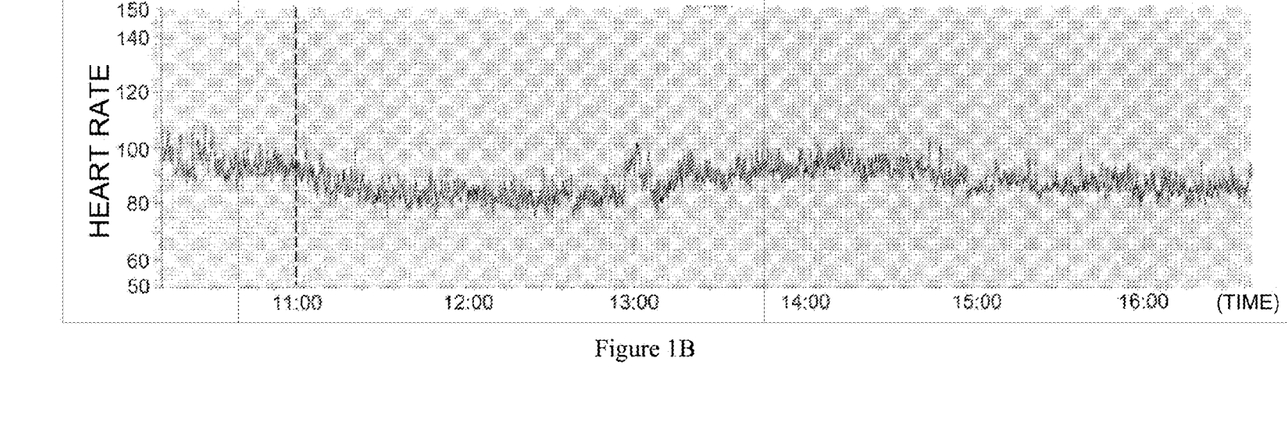

Incidentally, in this test, the oxygen concentration set to 12.4% to 12.7% increased to 13.9% at 30 minutes after the sublingual administration of orotic acid due to poor regulation of the oxygen concentration in the normobaric hypoxic room. However, thereafter, the oxygen concentration decreased to 12.9% within about 1 hour and 30 minutes and was stably kept at 12.9% to 13.0%. Since the SpO2 level of subject A was stably maintained at about 88% during the time when the oxygen concentration was 12.9% to 13.0%, it can be ascertained that the increase in the SpO2 level after sublingual administration of orotic acid was not due to the increase in the oxygen concentration in the room. In addition, as a result of having lunch at 13:00, the heart rate subsequently increased slightly, but, overall, there was no considerable irregularity in heart rate (see FIG. 1B). Therefore, the possibility that the increase in the SpO2 level was caused by the increase in heart rate was denied. In addition, although subject A had a sense of discomfort, such as slight sleepiness, that was felt to be caused by hypoxia immediately after entering the room, the sense of discomfort disappeared soon after ingestion of orotic acid, and subject A spent the rest of time until leaving the room as usual.

The results described above demonstrated that when orotic acid is sublingually administered to a human being having decreased arterial oxygen saturation, the arterial oxygen saturation is immediately increased, and the increased arterial oxygen saturation is then maintained for a long time.

Example 2: Effect 2 of Suppressing Decrease in Arterial Oxygen Saturation by Absorption of Orotic Acid Via Oral Mucosa

[Test Method 2]

Three subjects (man in his 60s [subject A: the same subject as that Example 1], man in his 50s [subject B], and woman in her 50s [subject C]) were subjected to a test according to the method described in [Test method 1] above. Subject A was subjected to examination of swallowing (oral administration) two tablets each containing 200 mg of free form orotic acid monohydrate (manufactured by Kyowa Hakko Bio Co., Ltd.) (400 mg of orotic acid in total) for comparison with sublingual administration. In this test, the oxygen concentration in the room was stable within a range of 12.4% to 12.7% throughout the test period.

[Result 2-1: Subject A]

Figure 2A:
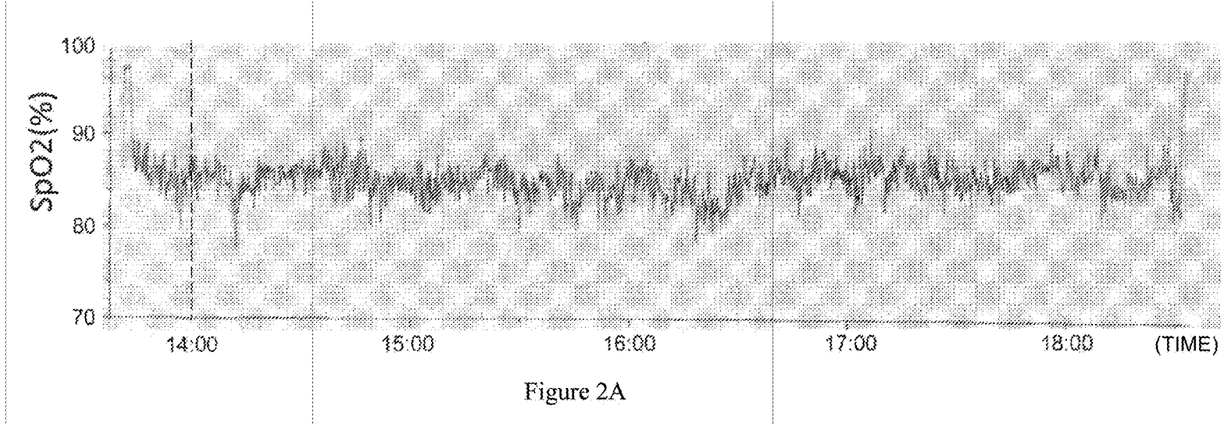
FIGS. 2A-B include graphs showing the results of measurement of SpO2 (FIG. 2A) and heart rate (FIG. 2B) of the subject A, where the measurement was performed in a normobaric hypoxic room before and after oral administration of orotic acid. The broken line in each graph indicates the time at which the orotic acid was orally administered.
Figure 2B:
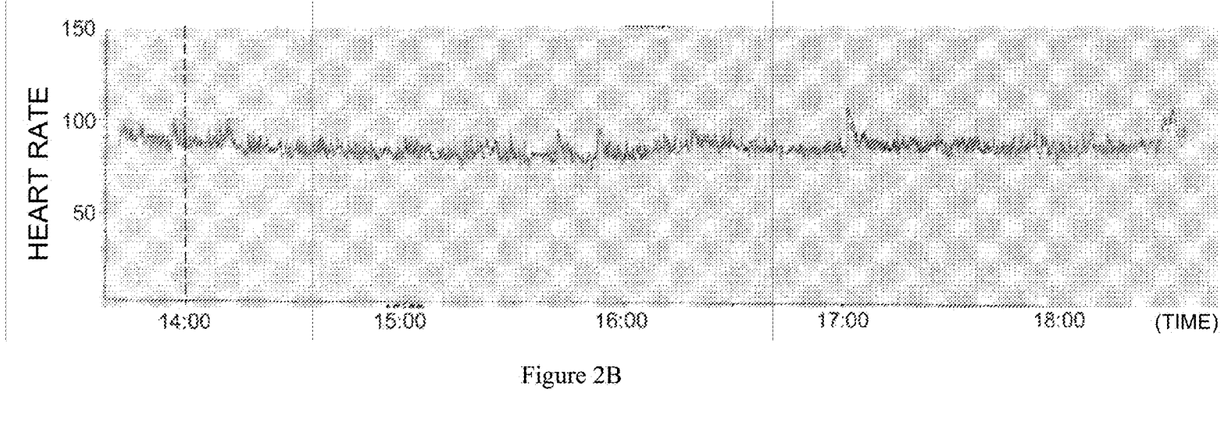

Subject A was orally administered with orotic acid at 30 minutes after entering the room (14:00). The SpO2 level decreased to 84% was hardly recovered (see FIG. 2A). In addition, the sense of discomfort that was felt to be caused by hypoxia after entering the hypoxic room was merely slightly improved. Incidentally, subject A did not have a considerable irregularity in heart rate throughout the test period (see FIG. 2B).

[Result 2-2: Subject B]

Figure 3A:
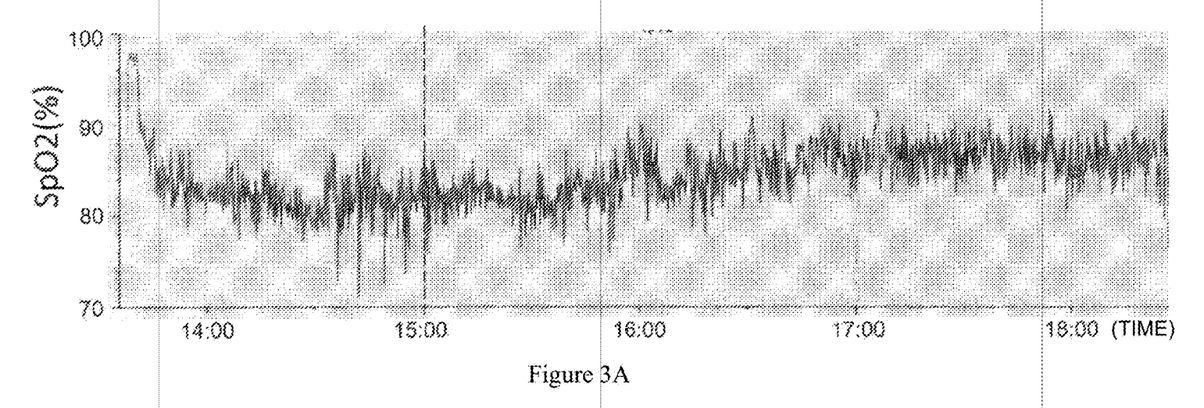
FIGS. 3A-B include graphs showing the results of measurement of SpO2 (FIG. 3A) and heart rate (FIG. 3B) of a subject B, where the measurement was performed in a normobaric hypoxic room before and after subligual administration of orotic acid. The broken line in each graph indicates the time at which the orotic acid was sublingually administered.
Figure 3B:
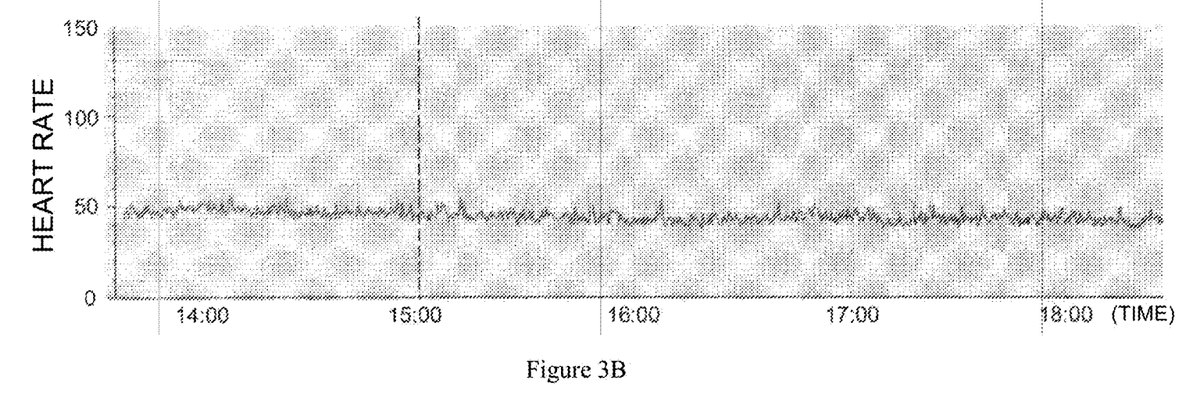

Subject B was sublingually administered with 400 mg of orotic acid at 1 hour and 30 minutes after entering the room (15:00). The SpO2 level decreased to 82% was increased at about 30 minutes after administration and was recovered to 86%, which was then stably maintained for at least 2 hours and 30 minutes until leaving the room (see FIG. 3A). In addition, subject B had symptoms, such as light sleepiness and reduced concentration, before administration of orotic acid, but such symptoms were cancelled by sublingual administration of orotic acid. Incidentally, since the heart rate of subject B hardly changed before and after administration of orotic acid (rather tended to slightly decrease) (see FIG. 3B), it was demonstrated that the increase in the SpO2 level after administration of orotic acid was not due to an increase in oxygen intake from the lung by the increase in the heart rate. The breathing of subject B did not change at all throughout the test period (no change was felt).

[Result 2-3: Subject C]

It was scheduled at first that subject C would be sublingually administered with orotic acid at 30 minutes after entering the room, but the SpO2 level after entering the room decreased to 70%, and headache and bad feeling were felt. Accordingly, in haste, 400 mg of orotic acid was sublingually administered at 20 minutes after entering the room. However, since being slightly rushed for ingestion, orotic acid was swallowed before dissolution of wafer paper, resulting in the same administration as oral administration. Thereafter, no recovery in the SpO2 level was observed. In this test in the hypoxic room, although it was required not to consciously change the breathing, subject C did not feel good, had light headache and frequent yawns, and could not read books. Accordingly, 200 mg of orotic acid was sublingually administered at 2 hours and 40 minutes after entering the room. After sublingual administration, the SpO2 level rapidly increased and was recovered to higher than 80%, and subject C felt better, the symptoms of altitude sickness, such as headache and bad feeling, disappeared, and subject C could also concentrate on crossword puzzles.

Example 3: Effect of Decreasing Energy Consumption after Exercise and Suppressing Increase in Uric Acid Level after Exercise by Absorption of Orotic Acid Via Oral Mucosa

[Test Method 3]

The compositions comprising the formulation ingredients shown in Table 1 were compressed into chewable tablets to manufacture orotic acid-containing throat candy and placebo throat candy.

TABLE 1

| Formulation ingredient | Orotic acid throat candy | | Placebo throat candy | |
|---|---|---|---|---|
| | mass (mg/piece) | content percentage (%) | mass (mg/piece) | content percentage (%) |
| Orotic acid[1] | 200 | 20.0 | — | — |
| Maltose | — | — | 200 | 20.0 |
| Grapefruit flavor | 13 | 1.3 | 13 | 1.3 |
| Citron peel powder | 3 | 0.3 | 3 | 0.3 |
| Citric acid | 40 | 4.0 | 40 | 4.0 |
| Aspartame | 2 | 0.2 | 2 | 0.2 |
| Sorbitol | 617 | 61.7 | 617 | 61.7 |
| Crystalline cellulose | 60 | 6.0 | 60 | 6.0 |
| Hydroxypropyl cellulose | 25 | 2.5 | 25 | 2.5 |
| Calcium stearate | 25 | 2.5 | 25 | 2.5 |
| Silicon dioxide | 15 | 1.5 | 15 | 1.5 |

[1]Free form orotic acid monohydrate, Lactoserum manufactured by Matsumoto Trading Co., Ltd.

Figure 4A:
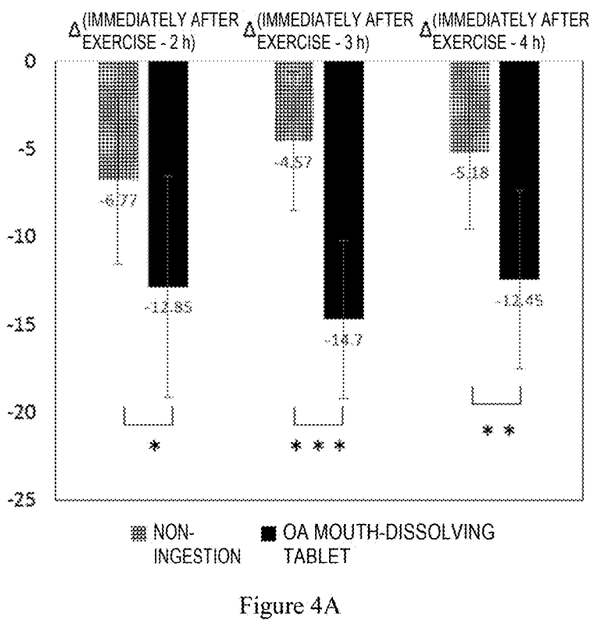
FIGS. 4A-B include graphs showing changes in energy consumption of healthy women who were administered with orotic acid by oral absorption administration or oral administration and then performed bike exercise. The graphs show comparison between ingestion of orotic acid-containing throat candy and ingestion of placebo throat candy (FIG. 4A) and comparison between oral administration of orotic acid and ingestion of placebo throat candy (FIG. 4B).
Figure 4B:
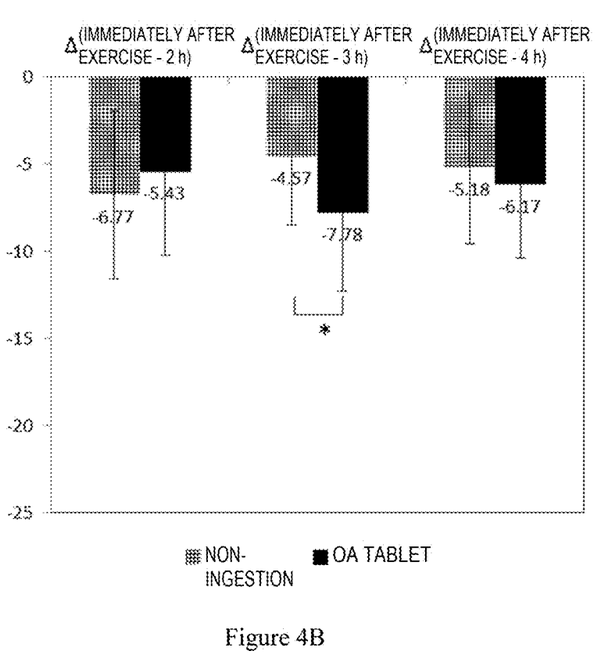
Figure 5:
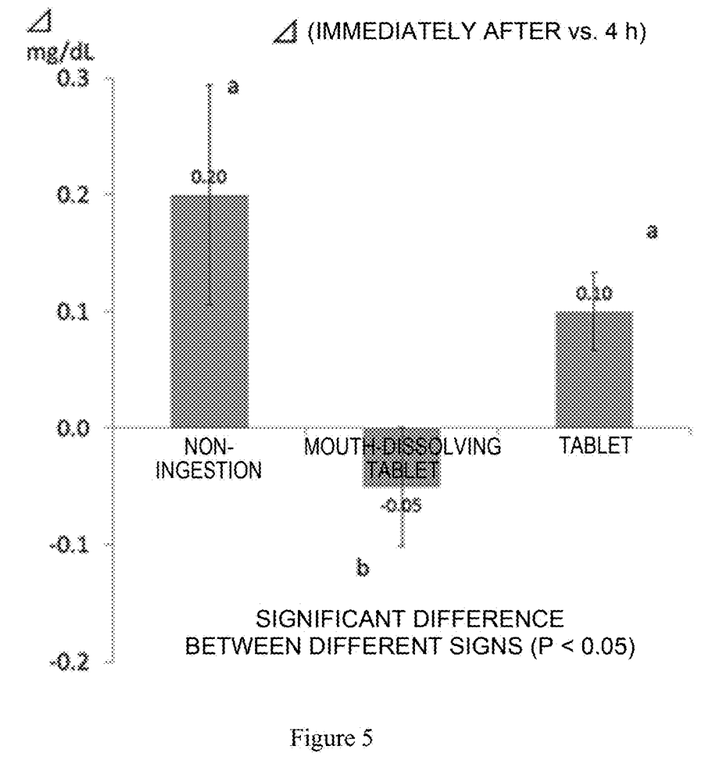
FIG. 5 is a graph showing the amounts of change in the uric acid level of healthy women who were administered with orotic acid by oral absorption administration or oral administration and then performed bike exercise.

Six 22-year-old healthy women were divided into three groups of two. All the women were fasted for 24 hours (allowed only to drink water or tea), and two women of one group ingested one tablet of the orotic acid-containing throat candy (OA mouth-dissolving tablet), two women of another group ingested one tablet of the free form orotic acid monohydrate-containing tablets manufactured in Example 2 (OA tablet), and two women of the remaining group ingested one tablet of the placebo throat candy (non-ingestion), and the women performed bike exercise (exercise intensity: 600 W) for 30 minutes. Changes in energy consumption and changes in plasma uric acid level were measured at 2 hours, 3 hours, and 4 hours after completion of the exercise by the following measuring method. The results are shown in FIGS. 4 and 5.

Method for Measuring Change in Energy Consumption

Exhalation was analyzed at immediately after completion of exercise and at 2 hours, 3 hours, and 4 hours after completion of exercise with AERO MONITOR AE 300S manufactured by Minato Medical Science Co., Ltd. Oxygen uptake volume and carbon dioxide production volume were measured, and the energy consumption (kcal/day) was determined by the following expression (1) to calculate the change in energy consumption.

$$\text{Energy consumption (kcal/day)} = (3.9 \times \text{oxygen uptake volume}) + (1.1 \times \text{carbon dioxide production volume}) \quad (1)$$

Method for Measuring Change in Plasma Uric Acid Level

The uric acid concentrations (mg/dL) at immediately after completion of exercise and at 4 hours after completion of exercise were determined by allowing peroxidase (POD) to act on hydrogen peroxide ($H_2O_2$), generated by oxidative decomposition of uric acid in a sample by the action of uricase, in the presence of 4-aminoantipyrine (4-AA) and a color former for oxidative condensation to generate a quinone dye (uricase-POD method). The resulting quinone dye is colorimetrically measured to calculate the change in plasma uric acid level.

[Result 3-1: Change in Energy Consumption]

The energy consumptions at 2 hours, 3 hours, and 4 hours after completion of bike exercise were decreased by ingestion of orotic acid compared to the energy consumption at immediately after the bike exercise. This effect when orotic acid was ingested by oral absorption as throat candy was remarkable compared to that when orotic acid was ingested by oral administration. It is presumed that the decrease in SpO2 level through exercise is suppressed by ingestion of orotic acid via oral mucosa before starting the exercise and as a result, the decrease in metabolism efficiency is also suppressed to decrease the energy consumption after the exercise.

[Result 3-2: Change in Plasma Uric Acid Level]

The change of the uric acid concentrations at immediately after exercise and at 4 hours after completion of the exercise was an increase of 0.2 mg/dL in the group in which orotic acid was not ingested (the left side of FIG. 5), an increase of 0.1 mg/dL in the group in which orotic acid was ingested by oral administration (the right side of FIG. 5), and a decrease of 0.05 mg/dL in the group in which orotic acid was ingested by oral absorption as throat candy (the center of FIG. 5). Accordingly, it was revealed that when exercise was performed after ingestion of orotic acid, the increase in plasma uric acid level after the exercise was suppressed and that this effect was remarkable in ingestion by oral absorption of orotic acid compared to that in ingestion by oral administration. It is presumed that ingestion of orotic acid via oral mucosa before starting exercise suppresses a decrease in SpO2 level by the exercise and as a result, an increase in plasma uric acid level is suppressed, or plasma uric acid level is decreased.

Example 4: Effect of Suppressing Decrease in Arterial Oxygen Saturation by Absorption of Orotic Acid Via Oral Mucosa

[Test Method 4]

A 70-year old woman with idiopathic pulmonary fibrosis ingested two tablets of the orotic acid-containing throat candy manufactured in Example 3 and then ingested one tablet of the throat candy every day for 4 weeks, and SpO2 was measured by the method described in Example 1.

[Result 4]

Although the SpO2 levels at immediately before the ingestion of the throat candy were about 91%, the SpO2 level was increased to about 93% at 30 minutes after ingestion of two tablets of the throat candy. The SpO2 levels at 2 weeks and 4 weeks after the ingestion of two tablets of the throat candy was maintained at 93% to 94%, the amount of phlegm was reduced by half, and the pulse was stabilized at 100 or less.

Example 5: Effect of Suppressing Decrease in Arterial Oxygen Saturation by Absorption of Orotic Acid Via Oral Mucosa

[Test Method 5]

Figure 6:
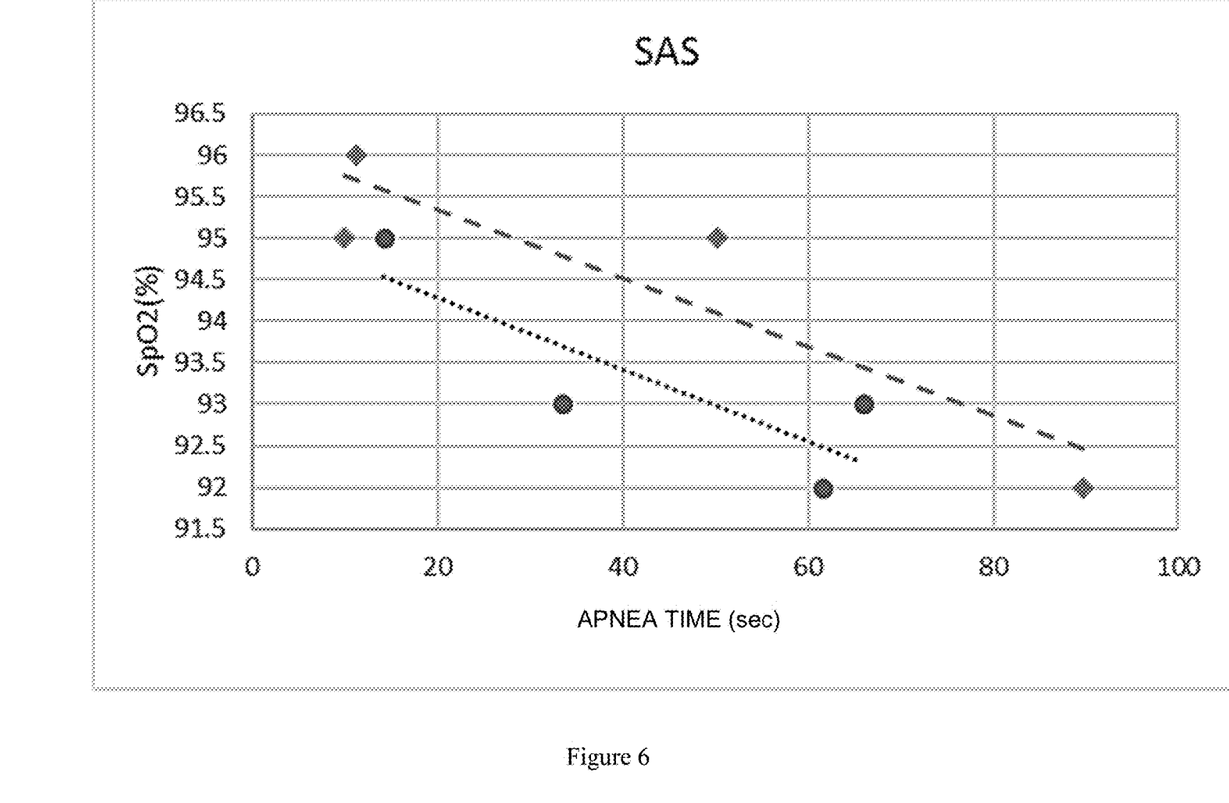
FIG. 6 is a graph showing SpO2 of women suspected of having sleep apnea syndrome at an apnea or hypopnea state.

A 57-year old woman suspected of having sleep apnea syndrome (SAS) ingested one tablet of the placebo throat candy manufactured in Example 3 at bedtime, and the maximum time of sleep apnea (a state in which breathing stops for 10 seconds of more) or hypopnea (a state in which ventilation by breathing falls to 50% or less for 10 seconds or more), which are detected with testing equipment for sleep apnea syndrome lent from a medical corporation Koshikai Ginza Yasue Clinic, and the SpO2 level at that time was measured two nights by the method in Example 1 (these levels are written by numerical numbers in the diagnostic results analyzed by the clinic software). The women then ingested one tablet of the orotic acid-containing throat candy manufactured in Example 3 at bedtime, and the maximum time of sleep apnea or hypopnea state and the SpO2 level at that time was measured by the same method as above two nights. The results are shown in FIG. 6. In FIG. 6, the results in ingestion of one tablet of placebo throat candy are shown by round-shaped plots, and the results in ingestion of one tablet of orotic acid-containing throat candy are shown by diamond-shaped plots.

It was revealed that when the apnea time when orotic acid was ingested by oral absorption as throat candy and the apnea time when orotic acid was not ingested were the same, the SpO2 level when orotic acid was ingested via oral mucosa was higher than that when orotic acid was not ingested. Accordingly, an effect of reducing hypoxia by ingestion of orotic acid via oral mucosa is expected.

Figure 7:
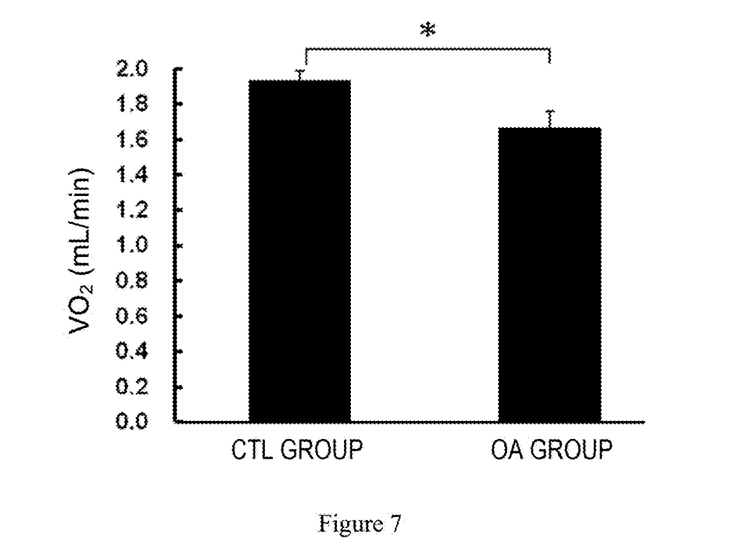
FIG. 7 is a graph showing the results of analysis of oxygen consumption (VO2) in mice during non-exercise in the test of reference example 1. "*" represents that the orotic acid administration group (OA group) has a significant difference with respect to the control group (CTL group) at a risk rate of less than 5%.
Figure 8:
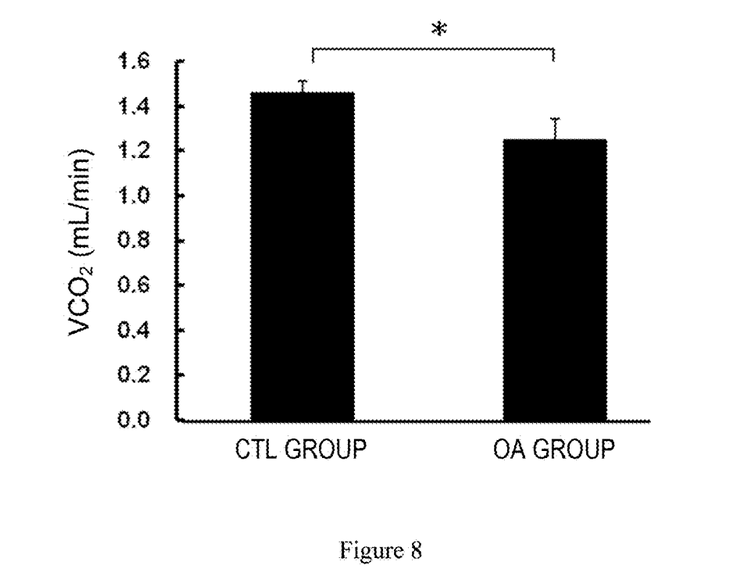
FIG. 8 is a graph showing the results of analysis of carbon dioxide production volume (VCO2) in mice during non-exercise in the test of reference example 1. The asterisk "*" represents that the orotic acid administration group (OA group) has a significant difference with respect to the control group (CTL group) at a risk rate of less than 5%.
Figure 9:
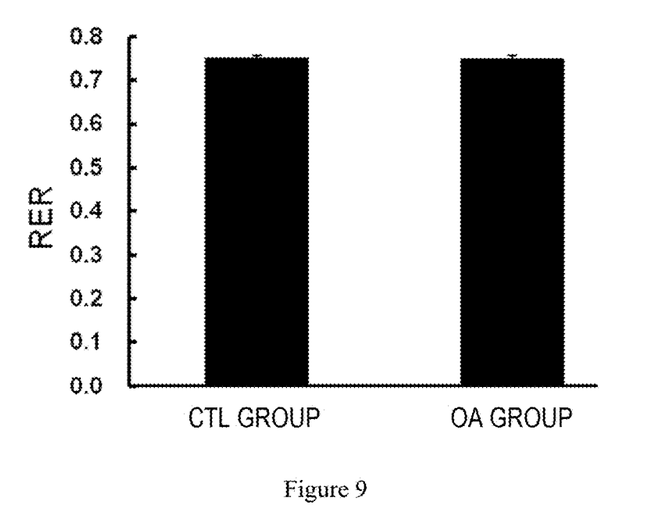
FIG. 9 is a graph showing the results of analysis of respiratory quotient (RER) in mice during non-exercise in the test of reference example 1.

Reference Example 1: Effect of Decreasing Oxygen Consumption During Non-Exercise by Oral Ingestion of Orotic Acid In order to verify whether orotic acid has an effect of decreasing the oxygen consumption during non-exercise or not, the following test was performed. Thirty-two ddY male mice (6-week old) bred in a thermostatic animal chamber of 24±2° C. for one week or more under a light-dark cycle of 12 hours (lighting from 8:00 to 20:00) were prepared. These mice were divided into two groups. Each mouse in one group (control group: CTL group) was administered with 0.5 mass % carboxymethyl cellulose solution (CMC solution) in an amount of 10 mL per 1 kg of mouse body weight. Each mouse in the other group (orotic acid administration group: OA group) was administered with orotic acid (50 mg/mL) suspended in 0.5 mass % CMC solution in an amount of 10 mL per 1 kg of mouse body weight. These administrations were performed 5 times a week for successive 4 weeks (20 times in total) for each mouse. Each mouse was transferred to a metabolism measurement chamber at 19:00 on the day of last administration to start fasting, and the oxygen consumption ($VO_2$ [mL/min]) and carbon dioxide production volume ($VCO_2$ [mL/min]) during the dark period from 20:00 to 8:00 on the following day were measured. FIG. 7 shows the average value of the oxygen consumption in each group, and FIG. 8 shows the average value of the carbon dioxide production volumes in each group. Incidentally, for statistical processing, t-test was used, and items that showed a significant difference at $p<0.05$ were indicated by asterisk *. In addition, the respiratory quotient (RER) of each mouse was calculated as a value obtained by dividing the carbon dioxide production volume by the oxygen consumption. FIG. 9 shows the average value of the respiratory quotients in each group.

As shown in FIGS. 7 and 8, the oxygen consumption and the carbon dioxide production volume in the orotic acid administration group were significantly decreased compared to those in the control group. On the other hand, regarding the respiratory quotient, there was not a significant difference between the orotic acid administration group and the control group (see FIG. 9). It was revealed from the above that oral ingestion of orotic acid has an effect of decreasing oxygen consumption during non-exercise without changing the respiratory quotient at that time.

Figure 10:
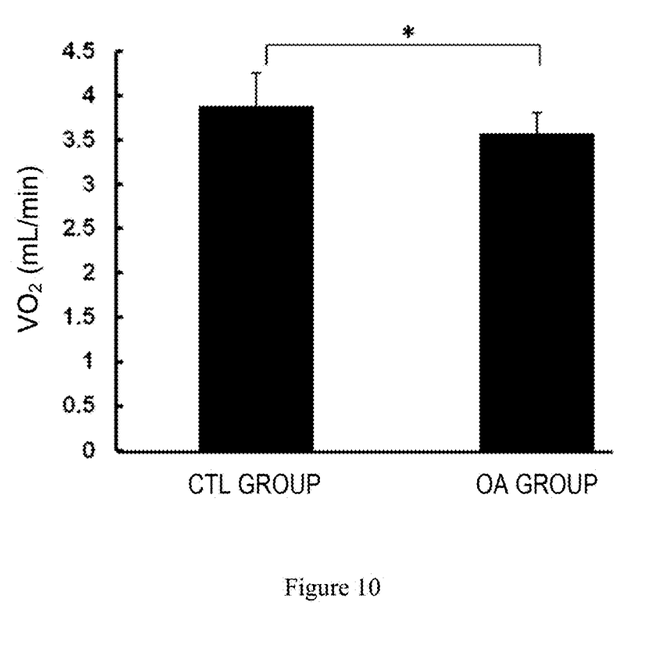
FIG. 10 is a graph showing the results of analysis of oxygen consumption (VO2) in mice during exercise in the test of reference example 2. The asterisk "*" represents that the orotic acid administration group (OA group) has a significant difference with respect to the control group (CTL group) at a risk rate of less than 5%.
Figure 11:
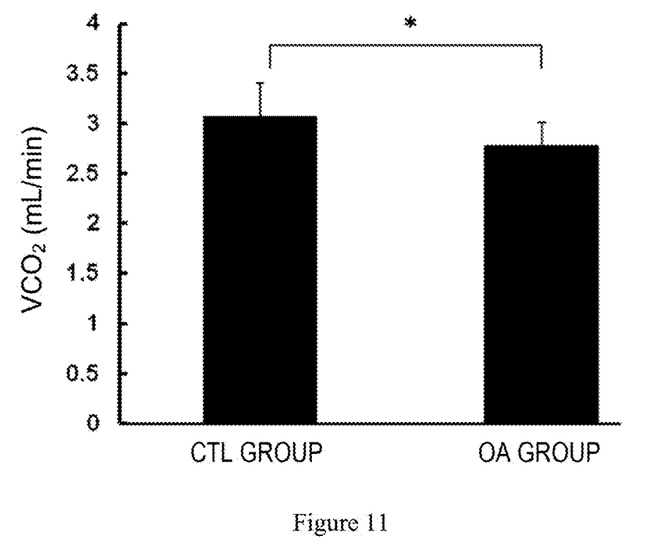
FIG. 11 is a graph showing the results of analysis of carbon dioxide production volume (VCO2) in mice during exercise in the test of reference example 2. The asterisk "*" represents that the orotic acid administration group (OA group) has a significant difference with respect to the control group (CTL group) at a risk rate of less than 5%.
Figure 12:
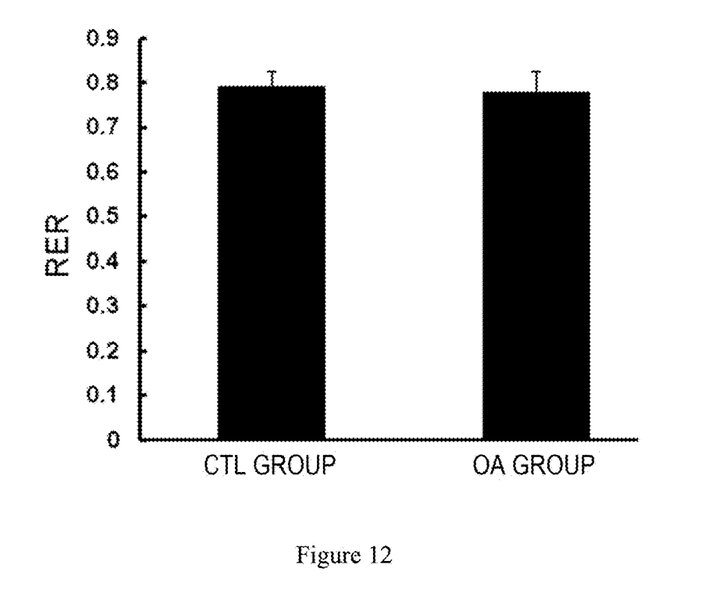
FIG. 12 is a graph showing the results of analysis of respiratory quotient (RER) in mice during exercise in the test of reference example 2.

Reference Example 2: Effect of Decreasing Oxygen Consumption During Exercise by Oral Ingestion of Orotic Acid In order to verify whether orotic acid has an effect of decreasing the oxygen consumption during exercise or not, the following test was performed. Twenty-four ddY male mice (6-week old) bred in a thermostatic animal chamber of 24±2° C. for one week or more under a light-dark cycle of 12 hours (lighting from 8:00 to 20:00) were prepared. These mice were divided into two groups. Each mouse in one group, CTL group, was administered with 0.5 mass % CMC solution in an amount of 10 mL per 1 kg of mouse body weight. Each mouse in the other group, OA group, was administered with 50 mg/mL of orotic acid suspended in 0.5 mass % CMC solution in an amount of 10 mL per 1 kg of mouse body weight. These administrations were performed 5 times a week for successive 3 weeks (15 times in total) for each mouse. Fasting of each mouse was started at 17:00 on the day of last administration. The mice were subjected to forced exercise using a mouse treadmill from 10:00 on the following day, and the oxygen consumption and the carbon dioxide production volume during exercise were measured. Incidentally, the forced exercise was performed for 30 minutes in total at a speed of 15 m/min for first 5 minutes, at a speed of 20 m/min for the following 5 minutes, and then at a speed of 25 m/min for 20 minutes. FIG. 10 shows the average value of the oxygen consumption in each group, and FIG. 11 shows the average value of the carbon dioxide production volumes in each group. Incidentally, for statistical processing, t-test was used, and items that showed a significant difference at $p<0.05$ were indicated by asterisk *. In addition, the respiratory quotient of each mouse was calculated as a value obtained by dividing the carbon dioxide production volume by the oxygen consumption. FIG. 12 shows the average value of the respiratory quotients in each group.

As shown in FIGS. 10 and 11, the oxygen consumption and the carbon dioxide production volume in the orotic acid administration group were significantly decreased compared to those in the control group. On the other hand, regarding the respiratory quotient, there was not a significant difference between the orotic acid administration group and the control group (see FIG. 12). It was revealed from the above that orotic acid has an effect of decreasing oxygen consumption during exercise without changing the respiratory quotient at that time.

The results of reference examples 1 and 2 demonstrated that orotic acid has an effect of decreasing oxygen consumption regardless of resting or exercising without changing the respiratory quotient at that time.

Reference Example 3: Effect of Enhancing Durability (Endurance) by Oral Ingestion of Orotic Acid The endurance-enhancing effect was verified using orotic acid as a test substance. Seven-week old male ddY mice were purchased from Japan SLC, Inc. and were each acclimatized for 7 days and then forced to swim with a weight on the tail. When a mouse could not come up to the water surface and stayed under the surface of the water for 5 seconds, the time thereof was measured as the limit swimming time. The mice were divided into groups, such that there was no difference in limit swimming time between the groups, as follows: control group (CTL group, n=10), orotic acid 250 mg/kg administration group (OA 250 mg/kg group, n=10), and orotic acid 500 mg/kg administration group (OA 500 mg/kg group, n=10). The mice in each group were bred using roughage (CE-2), and the mice in OA 250 mg/kg group and OA 500 mg/kg group were orally administered with 250 mg/kg of orotic acid and 500 mg/kg of orotic acid, respectively, five times a week. After the grouping, the limit swimming time in each group was measured once a week while being bred for 3 weeks. The measured limit swimming times are shown in FIG. 13.

Figure 13:
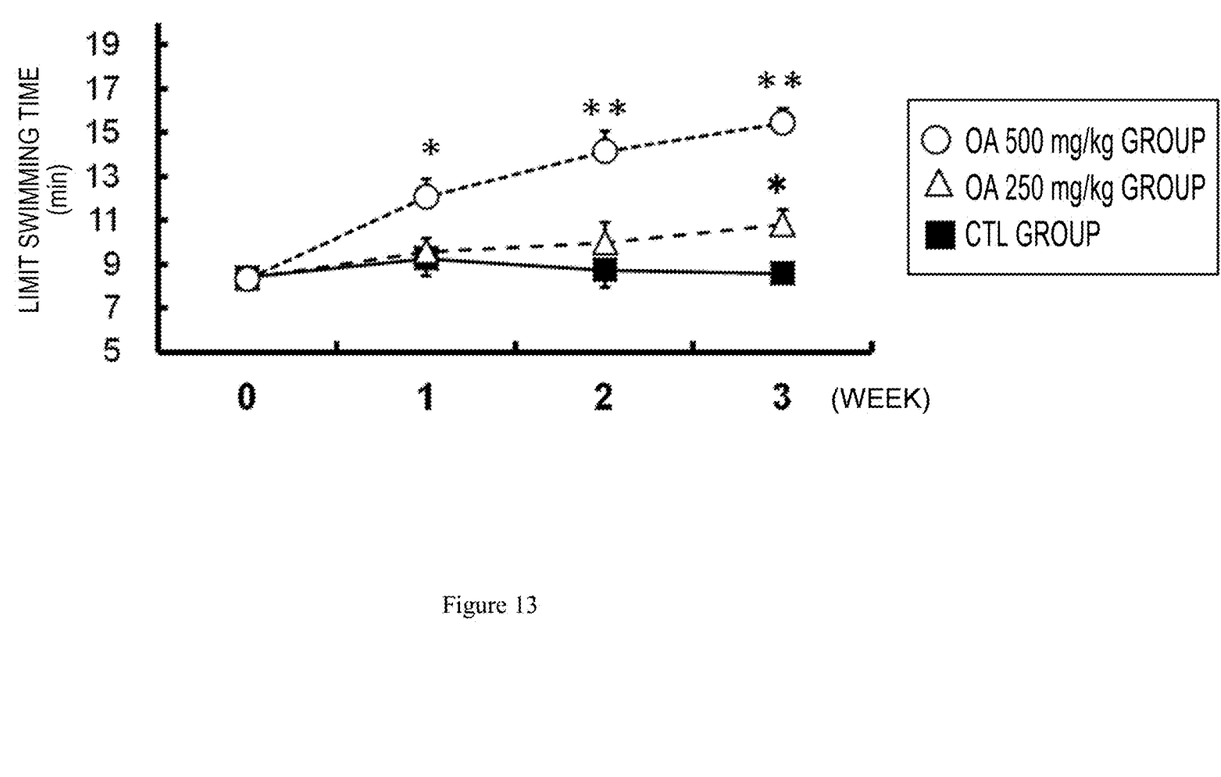
FIG. 13 is a graph showing the results of analysis of limit swimming time in mice in the test of reference example 3. The asterisks "*" and "**" represent that each group has a significant difference with respect to the control group (CTL group) at a risk rate of less than 5% and a risk rate of less than 1%, respectively.

As shown by the results drawn in FIG. 13, in the mice orally administered with orotic acid, the limit swimming time was prolonged depending on the dose of orotic acid, and it could be confirmed that orotic acid has an endurance-enhancing effect. The results in reference examples 1 to 3 revealed that orotic acid has an effect of decreasing oxygen consumption and energy consumption and also has an endurance-enhancing effect (energy-saving effect).

Conclusion

Regarding the administration method of orotic acid to subject A, in comparison between the first administration by a sublingual route and the second administration by an oral route, an effect of immediately increasing decreased arterial oxygen saturation and persistence of the effect were observed in the sublingual administration (not the oral administration) (see Examples 1 and 2). Similarly, also in subjects B and C, an effect of immediately increasing decreased arterial oxygen saturation and persistence of the effect were observed by sublingual administration of orotic acid (see Examples 2 and 3). In subject C, as in subject A, the immediate effect of orotic acid was not observed in the first administration by an oral route and was observed in the following administration by a sublingual route.

The results described above demonstrate that a decrease in arterial oxygen saturation can be effectively prevented or improved by absorption of orotic acid into the body via oral mucosa by a method such as sublingual administration and that the effect can be maintained for a long time.

The experiments using mice confirmed that an energy-saving effect is obtained by oral administration of orotic acid for 3 weeks or more (see reference examples 1 to 3). It is conceivable that a large amount of orotic acid is used (disappears) in the intestine and the liver when the orotic acid is orally administered, but when the orotic acid is absorbed into the body via oral mucosa, since the blood orotic acid level rapidly increases, an energy-saving effect by a decrease in the oxygen demand in the brain, muscle, etc. is recognized.

In the experiments using mice, oral administration of orotic acid needed at least three weeks for obtaining a significant difference, and the effect was not observed on the day of administration or within one week after the administration. This is the first time that the effect of immediately increasing decreased arterial oxygen saturation by absorption of orotic acid into the body via oral mucosa has been found. This is important not only in that the energy-saving effect observed in mice was reproduced in humans, but also in that it was found that the effect was obtained on the same day as the oral sublingual absorption of orotic acid. That is, it is demonstrated that ingestion of orotic acid in advance is effective even in situations where subsequent temporary hypoxia is predicted, such as humans before exercise or sleep apnea syndrome humans before sleeping. No biological component having such an effect or its ingestion method has been found so far.

INDUSTRIAL APPLICABILITY

The present invention contributes to prevention or improvement of a symptom or disease related to hypoxia or an increase in blood uric acid level, improvement of performance in sports where high-altitude training or hypoxic training is effective, and a field of manufacturing foods (for example, health foods and foods with health claims) and pharmaceutical products intended to recover from fatigue due to exercise and reduce the fatigue.

The invention claimed is:

1. A method for suppressing a decrease in arterial oxygen saturation or for increasing decreased arterial oxygen saturation, comprising administering by oral mucosa administration orotic acid or a salt thereof to a subject in need of suppressing a decrease in arterial oxygen saturation, or a subject whose arterial oxygen saturation is decreased so that the orotic acid or a salt thereof is absorbed into the body via oral mucosa.

2. The method according to claim 1, wherein the decrease in arterial oxygen saturation is caused by breathing in air with reduced oxygen concentration, reduced cardiopulmonary function, or respiratory arrest.

3. The method according to claim 1, wherein the decrease in arterial oxygen saturation is caused by exercise.

4. The method according to claim 1, wherein the decrease in arterial oxygen saturation is caused by alcohol drinking.

5. The method according to claim 1, wherein the orotic acid or a salt thereof is administered in admixture with carnitine.

6. The method according to claim 1, wherein the orotic acid or a salt thereof is a sublingual tablet.

7. The method according to claim 1, wherein the orotic acid or a salt thereof is administered at a dose of 200 mg/day.

8. The method according to claim 2, wherein the orotic acid or a salt thereof is administered in admixture with carnitine.

9. The method according to claim 3, wherein the orotic acid or a salt thereof is administered in admixture with carnitine.

10. The method according to claim 4, wherein the orotic acid or a salt thereof is administered in admixture with carnitine.

11. The method according to claim 2, wherein the orotic acid or a salt thereof is a sublingual tablet.

12. The method according to claim 3, wherein the orotic acid or a salt thereof is a sublingual tablet.

* * * * *